United States Patent
Choi et al.

(10) Patent No.: US 11,000,365 B2
(45) Date of Patent: May 11, 2021

(54) MULTIFOCAL DIFFRACTIVE OPHTHALMIC LENS USING SUPPRESSED DIFFRACTIVE ORDER

(71) Applicant: NOVARTIS AG, Basel (CH)

(72) Inventors: Myoung-Taek Choi, Arlington, TX (US); Xin Hong, Fort Worth, TX (US); Yueai Liu, Arlington, TX (US)

(73) Assignee: Alcon Inc., Fribourg (CH)

( * ) Notice: Subject to any disclaimer, the term of this patent is extended or adjusted under 35 U.S.C. 154(b) by 38 days.

(21) Appl. No.: 16/371,395

(22) Filed: Apr. 1, 2019

(65) Prior Publication Data

US 2019/0224000 A1 Jul. 25, 2019

Related U.S. Application Data

(63) Continuation of application No. 15/095,253, filed on Apr. 11, 2016, now Pat. No. 10,278,811, which is a continuation of application No. 14/575,333, filed on Dec. 18, 2014, now Pat. No. 9,335,564.

(60) Provisional application No. 61/993,892, filed on May 15, 2014.

(51) Int. Cl.
| | |
|---|---|
| *A61F 2/16* | (2006.01) |
| *G02C 7/06* | (2006.01) |
| *G02B 5/18* | (2006.01) |
| *G02C 7/04* | (2006.01) |

(52) U.S. Cl.
CPC .......... *A61F 2/1654* (2013.01); *A61F 2/1618* (2013.01); *G02B 5/1876* (2013.01); *G02C 7/042* (2013.01); *G02C 7/06* (2013.01); *A61F 2230/0006* (2013.01); *G02C 2202/20* (2013.01)

(58) Field of Classification Search
CPC .................................................. A61F 2/1654
See application file for complete search history.

(56) References Cited

U.S. PATENT DOCUMENTS

| | | | |
|---|---|---|---|
| 8,500,805 B2 | 8/2013 | Kobayashi et al. | |
| 9,335,564 B2 | 5/2016 | Choi et al. | |
| 2009/0187242 A1* | 7/2009 | Weeber | G02B 27/0075 623/6.24 |

(Continued)

FOREIGN PATENT DOCUMENTS

| | | |
|---|---|---|
| EP | 0605841 A1 | 7/1994 |
| EP | 2377493 B1 | 8/2015 |

(Continued)

OTHER PUBLICATIONS

Alfonso, et al., "Intermediate visual function with different multifocal intraocular lens models", J. Cataract Refract. Surg., 2010, 36:733-739.

*Primary Examiner* — Leslie Lopez

(57) ABSTRACT

A multifocal ophthalmic lens includes an ophthalmic lens and a diffractive element. The ophthalmic lens has a base curvature corresponding to a base power. The diffractive element produces constructive interference in at least four consecutive diffractive orders corresponding a range of vision between near and distance vision. The constructive interference produces a near focus, a distance focus corresponding to the base power of the ophthalmic lens, and an intermediate focus between the near focus and the distance focus. A diffraction efficiency of at least one of the diffractive orders is suppressed to less than ten percent.

18 Claims, 4 Drawing Sheets

(56) References Cited

U.S. PATENT DOCUMENTS

| | | |
|---|---|---|
| 2009/0268155 A1 | 10/2009 | Weeber |
| 2010/0100178 A1 | 4/2010 | Weeber et al. |
| 2011/0270390 A1 | 11/2011 | Kobayashi et al. |
| 2012/0140166 A1 | 6/2012 | Zhao |
| 2012/0224138 A1 | 9/2012 | Cohen |
| 2015/0022775 A1 | 1/2015 | Ando |

FOREIGN PATENT DOCUMENTS

| | | |
|---|---|---|
| WO | 94/11765 A1 | 5/1994 |
| WO | 2006/023404 A2 | 3/2006 |
| WO | 2010/093975 A2 | 8/2010 |
| WO | 2011/134948 A1 | 11/2011 |
| WO | 2013/118499 A1 | 8/2013 |

* cited by examiner $(x=r^2)$

| Embodiment #1 | Ring 1 | Ring 2 | Ring 3 |
|---|---|---|---|
| Height (wave) | 0.60809 | 0.49816 | -0.44179 |
| Phase (wave) | -0.304 | -0.249 | 0.221 |

| Embodiment #1 | 0th Order | 1st Order | 2nd Order | 3rd Order |
|---|---|---|---|---|
| Diffraction Efficiency (%) | 38 | 5 | 13 | 16 |

FIG. 3

| Embodiment #2 | Ring 1 | Ring 2 | Ring 3 |
|---|---|---|---|
| Height (wave) | 0.56726 | -0.35995 | 0.59204 |
| Phase (wave) | -0.284 | 0.180 | -0.296 |

| Embodiment #2 | 0th Order | 1st Order | 2nd Order | 3rd Order |
|---|---|---|---|---|
| Diffraction Efficiency (%) | 39 | 3 | 12 | 18 |

FIG. 4

| Embodiment #3 | Ring 1 | Ring 2 | Ring 3 |
|---|---|---|---|
| Height (wave) | 0.62956 | 0.32692 | 0.19913 |
| Phase (wave) | 0 | 0 | 0 |

| Embodiment #3 | 0th Order | 1st Order | 2nd Order | 3rd Order |
|---|---|---|---|---|
| Diffraction Efficiency (%) | 44 | 7 | 14 | 16 |

FIG. 5

| Embodiment #4 | Ring 1 | Ring 2 | Ring 3 |
|---|---|---|---|
| Height (wave) | 0.43779 | 0.22281 | 0.64954 |
| Phase (wave) | 0 | 0 | 0 |

| Embodiment #4 | 0th Order | 1st Order | 2nd Order | 3rd Order |
|---|---|---|---|---|
| Diffraction Efficiency (%) | 37 | 6 | 16 | 23 |

FIG. 6

| Embodiment #5 | Ring 1 | Ring 2 | Ring 3 |
|---|---|---|---|
| Height (wave) | 0.45236 | 0.15970 | 0.61195 |
| Phase (wave) | 0 | 0.059 | 0.03628 |

| Embodiment #5 | 0th Order | 1st Order | 2nd Order | 3rd Order |
|---|---|---|---|---|
| Diffraction Efficiency (%) | 40 | 6 | 16 | 21 |

FIG. 7

| Embodiment #6 | Ring 1 | Ring 2 | Ring 3 |
|---|---|---|---|
| Height (wave) | 0.61518 | 0.44118 | -0.00806 |
| Phase (wave) | 0 | -0.03516 | 0.18421 |

| Embodiment #6 | 0th Order | 1st Order | 2nd Order | 3rd Order |
|---|---|---|---|---|
| Diffraction Efficiency (%) | 49 | 3 | 15 | 17 |

FIG. 8

MULTIFOCAL DIFFRACTIVE OPHTHALMIC LENS USING SUPPRESSED DIFFRACTIVE ORDER

TECHNICAL FIELD

The present invention relates generally to multifocal ophthalmic lenses and more specifically to a multifocal diffractive ophthalmic lens with a suppressed diffractive order.

BACKGROUND

The human eye functions to provide vision by refracting light through a clear outer portion called the cornea, and refracting the light by way of a crystalline lens onto a retina. The quality of the focused image depends on many factors including the size and shape of the eye, and the transparency of the cornea and the lens. When age or disease causes the lens to become aberrated, vision deteriorates because of the loss of retinal image quality. This loss of optical quality in the lens of the eye is medically known as a cataract. An accepted treatment for this condition is surgical removal of the lens and replacement of the lens function by an artificial intraocular lens (IOL). As the eye ages, it may also lose the ability to change focus to nearer focal points, known as accommodation. This loss of accommodation with age is known as presbyopia.

In the United States, the majority of cataractous lenses are removed by a surgical technique called phacoemulsification. During this procedure, a portion of the anterior capsule is removed and a thin phacoemulsification cutting tip is inserted into the diseased lens and vibrated ultrasonically. The vibrating cutting tip liquefies or emulsifies the nucleus and cortex of the lens so that the lens may be aspirated out of the eye. The diseased nucleus and cortex of the lens, once removed, is replaced by an artificial intraocular lens (IOL) in the remaining capsule (in-the-bag). In order to at least partially restore the patient's ability to see in focus at near distances, the implanted IOL may be a multifocal lens.

One common type of multifocal lens is a diffractive lens, such as a bifocal lens providing distance vision and near (or intermediate) vision. Trifocal diffractive lenses are also available that provide an additional focal point and, at least potentially, a broader range of in-focus vision. However, there are disadvantages associated with dividing light energy among multiple focal points, particularly in trifocal lenses. Thus, there remains a need for improved multifocal diffractive lenses.

SUMMARY

In various embodiments of the invention, a multifocal ophthalmic lens includes an ophthalmic lens and a diffractive element. The ophthalmic lens has a base curvature corresponding to a base power. The diffractive element produces constructive interference in at least four consecutive diffractive orders corresponding a range of vision between near and distance vision. The constructive interference produces a near focus, a distance focus corresponding to the base power of the ophthalmic lens, and an intermediate focus between the near focus and the distance focus. A diffraction efficiency of at least one of the diffractive orders is suppressed to less than ten percent.

Other features and advantages of various embodiments of the present invention will be apparent to one skilled in the art from the following description.

BRIEF DESCRIPTION OF THE DRAWINGS

FIGS. 3-8 are tables illustrating particular diffractive step arrangements according to particular embodiments of the present invention.

DETAILED DESCRIPTION

Various embodiments of the present invention provide a multifocal diffractive ophthalmic lens with at least one suppressed diffractive order. By suppression of one diffractive order, the performance of the lens can be tailored relative to conventional diffractive lenses. Known trifocal diffractive lenses, for example, divide light between multiple diffractive foci, such as (−1, 0, +1) order foci or (0, +1, +2) order foci.

By contrast, various embodiments of the present invention provide at least three foci corresponding to diffractive orders wherein at least one intermediate diffractive order is suppressed. This provides an intermediate focus that is closer either to distance vision or near vision, which provides a broader range of vision around the respective focus. Furthermore, suppression of the other intermediate order distributes more energy to the other foci, which may provide more useful vision. In the following description, the references to foci for an ophthalmic lens refer to a corresponding diffractive focus within the range of vision extending from ordinary near viewing around 30 cm to distance vision (essentially modeled as collinear light rays from infinite distance). This excludes spurious higher orders of diffractive lenses that lie outside the range of vision, which provide only unwanted light effects. Thus, for example, even diffractive lenses that are nominally bifocal include higher-order diffractive foci from constructive interference, but for purposes of this specification, those should not be considered foci of the ophthalmic lens.

In other embodiments, a multifocal diffractive lens produces foci corresponding to at least four consecutive diffractive orders including at least one focus less than one half of the near-most add power and at least one other focus greater than one half of the nearmost add power. This may be advantageous over conventional trifocal lenses, which have an add power that is half of the nearmost add power. This intermediate vision corresponds to twice the near-vision distance, so that if the near add-power corresponds to a working distance of 40 cm, a conventional reading distance, the intermediate viewing distance would be 80 cm. Given that a common intermediate working distance is at 60 cm, this would not provide a sharp focus at the most common working distance, which would fall between the near and intermediate foci. By contrast, a lens with a focus corresponding to ⅔ of the near add power would provide a focus at 60 cm, corresponding to the intermediate working distance.

Figure 1:
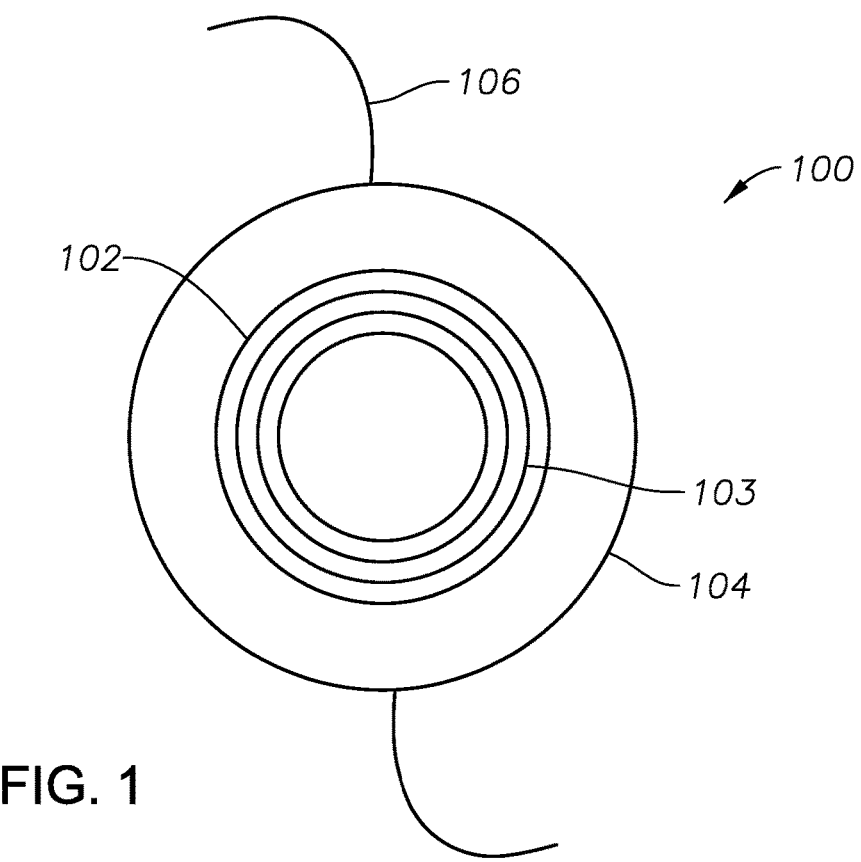
FIG. 1 illustrates an intraocular lens according to particular embodiments of the present invention.

FIG. 1 illustrates a particular embodiment of a multifocal diffractive ophthalmic lens (IOL) 100 including a diffractive element 102. The diffractive element 102 comprises diffractive steps 104 (also known as zones) having a characteristic radial separation to produce constructive interference at characteristic foci. In principle, any diffractive element that produces constructive interference through phase shifting in interfering zones, often referred to as a hologram, can be adapted for use in such a multifocal diffractive ophthalmic lens. Also, while the diffractive element is depicted with annular zones, the zones could conceivably be partial, such as semicircular or sectored zones, as well. While the following description will concern a diffractive element 102 including annular diffractive steps 103, it should be understood by those skilled in the art that suitable substitutions may be made in any embodiment discloses herein.

IOL 100 also includes an optic 104 on which the diffractive element 102 is located. The optic 104 determines the base optical power of the lens, which typically corresponds to the distance vision of the patient. This need not always the case; for example, a non-dominant eye may have an IOL with a base optical power is slightly less than the corresponding distance power for the patient to improve overall binocular vision for both eyes. Regardless, the add power for the IOL can be defined with respect to the base optical power. Haptics 106 hold the IOL 100 in place, providing stable fixation within the capsular bag. Although haptic arms are illustrated in the example, any suitable haptics fixation structure for the capsular bag or the ciliary sulcus compatible with posterior chamber implantation could also be used in a posterior chamber IOL.

Although the example below deals with a posterior chamber IOL 100, other ophthalmic lenses, including multifocal diffractive spectacles and multifocal diffractive contact lenses, could also benefit from the same approach. The known and fixed position of the lens relative to the optical axis makes such applications particularly advantageous for intraocular lenses, including intracorneal, anterior chamber, and posterior chamber lenses. However, this does not exclude the utility of multifocality in other applications.

Figure 2:
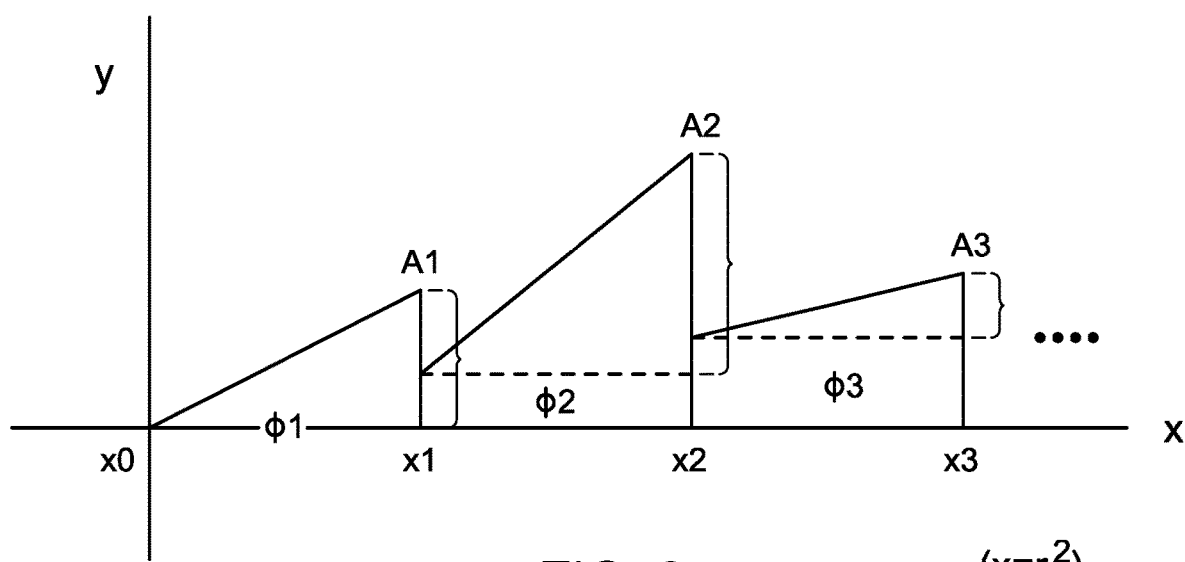
FIG. 2 illustrates a diffractive step arrangement according to particular embodiments of the present invention.

FIG. 2 illustrates, in more detail, a diffractive step structure useful for ophthalmic lenses such as the IOL 100 of FIG. 1. In particular, FIG. 2 illustrates a three-step repeating diffractive structure that produces a phase relationship for constructive interference at four different focal points within the range of vision. The step relationship at consecutive radial step boundaries along a scaled radial axis (x-axis), measured in $r^2$-space, is as follows:

$$y_i = \frac{A_i}{x_i - x_{i-1}}(x - x_{i-1}) + \phi_i$$

$$(i = 1, 2, 3)$$

wherein $A_i$ is the corresponding step height relative to the base curvature (base optical power) of the base lens (excluding the constant phase delay $\varphi_i$), $y_i$ is the sag in the corresponding segment (height above or below the x-axis), $\varphi_i$ is the relative phase delay from the x-axis, and $x_i$ is the position of the step along the x-axis. As will be apparent to one skilled in the art of diffractive optics, the radial position indicated in the formula is in $r^2$-space (i.e., parabolically scaled), as expected for zone spacing. In particular embodiments, the parameters are selected so that one of the foci is suppressed, which is to say that the light energy is reduced relative to the division among the foci such that the focused image is no longer visibly perceptible. This corresponds to a light energy of less than 10% of the incident light energy, as suggested by the fact that bifocal lenses with spurious diffractive orders of less than 10% of incident light energy do not result in separately perceptible images. The fraction of incident light energy focused at a particular order is referred to as the "diffraction efficiency."

The listed phase relationships are given with respect to the base curve determined by the base power of the IOL, corresponding to the zero-order diffractive focus for the lens. The radial spacing of the zones $x_i$ is ordinarily determined based on the ordinary Fresnel zone spacing in $r^2$-space as determined by the diffractive add power, although it can be varied to adjust the relative phase relationship between the components in ways known in the art to slightly modify the energy distribution between the foci. In the examples listed below, the spacing should be assumed to according to the known Fresnel pattern for producing four foci. This is analogous to the trifocal approach described in, e.g., U.S. Pat. Nos. 5,344,447 and 5,760,817 and PCT publication WO 2010/0093975, all of which are incorporated by reference. The diffractive steps can also be apodized (gradually reduced in step height relative to the nominal phase relationship) to reduce glare by progressively reducing the energy to the near focus in the manner described in U.S. Pat. No. 5,699,142.

FIGS. 3-8 provide example multifocal embodiments for a (0, +1, +2, +3) diffractive lens wherein the +1 order is suppressed. This advantageously provides an intermediate focus at ⅔ of the near add power, corresponding respectively to a focused image at 60 cm and 40 cm distance. Notably, the diffraction efficiency for the distance vision (zero-order) focus can be nearly 40%, comparable to the diffraction efficiency for conventional bifocal lenses, and the diffraction efficiency for the suppressed first-order focus can be less than 5%, while still providing visible intermediate and near foci at normal working distances of 60 cm and 40 cm, respectively. Compared to conventional multifocals, this better approximates the full range of working vision that a patient would use in the absence of the presbyopic condition.

Although particular embodiments have been described herein, one skilled in the art will appreciate that numerous variations are possible. In particular, the embodiments described herein are multifocal posterior chamber IOLs using (0, +1, +2, +3) diffractive orders with the +1 order being suppressed. This four-order embodiment could use different consecutive diffractive orders, such as starting with an order from −4 to −1, for example. And while it is desirable for the zero-order to be included for distance vision, that condition is not a necessary constraint. Lastly, the approach could be applied in principle to more than four diffractive orders; for example, a five-order diffractive lens could have add powers including two intermediate powers, a near power, and a suppressed intermediate power.

What is claimed is:

1. An intraocular lens, comprising:
    an ophthalmic lens having a base curvature corresponding to a base power; and
    a diffractive profile disposed on at least one of an anterior surface and a posterior surface, the diffractive profile comprising a plurality of annular zones configured to produce constructive interference in at least four consecutive diffractive orders corresponding to a range of vision; wherein:
        the four consecutive diffractive orders include a lowest diffractive order, a highest diffractive order, and two intermediate diffractive orders, and at least one of the two intermediate diffractive orders is suppressed;
        the constructive interference produces a near focus, a distance focus corresponding to the base power of the intraocular lens, and an intermediate focus, each corresponding to a different one of the four consecutive diffractive orders; and the lowest diffractive order of the consecutive diffractive orders corresponds to the distance focus; and
a diffraction efficiency of the lowest diffractive order is greater than a diffraction efficiency of any other of the consecutive diffractive orders.

2. The intraocular lens of claim 1, wherein a diffraction efficiency of at least one of the diffractive orders is suppressed to less than ten percent.

3. The intraocular lens of claim 2, wherein at least a portion of energy associated with the suppressed diffractive order is redistributed to one or more of the near focus, the intermediate focus, and the distance focus.

4. The intraocular lens of claim 1, wherein the four consecutive diffractive orders include at least two of the following diffractive orders: −4, −3, −2, −1, 0, +1, +2 and +3.

5. The intraocular lens of claim 1, wherein the distance focus corresponds to a 0th diffractive order.

6. The intraocular lens of claim 1, wherein the distance focus corresponds to a diffractive order other than the $0^{th}$ order.

7. The intraocular lens of claim 1, wherein the near focus corresponds to vision at 40 cm, and the intermediate focus corresponds to vision at 60 cm.

8. An intraocular lens, comprising:
an ophthalmic lens having a base curvature corresponding to a base power; and
a diffractive profile disposed on at least one of an anterior surface and a posterior surface, the diffractive profile comprising a plurality of annular zones configured to produce constructive interference in at least four consecutive diffractive orders corresponding a range of vision; wherein:
the constructive interference produces a near focus, a distance focus corresponding to the base power of the intraocular lens, a near-intermediate focus, and a far-intermediate focus, each corresponding to a different one of the four consecutive diffractive orders;
the near focus, the near-intermediate focus, and the far-intermediate focus each correspond to a different add power relative to the base power;
a first add power corresponding to the far-intermediate focus is less than one half of a third add power corresponding to the near focus; and
a second add power corresponding to the near-intermediate focus is greater than one half of the third add power corresponding to the near focus.

9. The intraocular lens of claim 8, wherein
the four consecutive diffractive orders include a lowest diffractive order, a highest diffractive order, and two intermediate diffractive orders; and
at least one of the consecutive diffractive orders is suppressed.

10. The intraocular lens of claim 9, wherein
the at least one suppressed diffractive order is one of the two intermediate diffractive orders.

11. The intraocular lens of claim 10, wherein at least a portion of energy associated with the at least one suppressed diffractive order is redistributed to one or more of the near focus, the intermediate focus, and the distance focus.

12. The intraocular lens of claim 8, wherein
the four consecutive diffractive orders include a lowest diffractive order, a highest diffractive order, and two intermediate diffractive orders; and
a diffraction efficiency of the lowest diffractive order is greater than a diffraction efficiency of any other of the consecutive diffractive orders.

13. The intraocular lens of claim 8, wherein the four consecutive diffractive orders include at least two of the following diffractive orders: −4, −3, −2, −1, 0, +1, +2 and +3.

14. The intraocular lens of claim 8, wherein the distance focus corresponds to a $0^{th}$ diffractive order.

15. The intraocular lens of claim 8, wherein the distance focus corresponds to a diffractive order other than the $0^{th}$ order.

16. The intraocular lens of claim 8, wherein the plurality of annular zones comprises a plurality of repeating diffractive steps.

17. An intraocular lens, comprising:
an ophthalmic lens having a base curvature corresponding to a base power; and
a diffractive profile disposed on at least one of an anterior surface and a posterior surface, the diffractive profile comprising a plurality of annular zones configured to produce constructive interference in at least four consecutive diffractive orders corresponding to a range of vision; wherein:
the constructive interference produces a near focus, a distance focus corresponding to the base power of the intraocular lens, and an intermediate focus, each corresponding to a different one of the four consecutive diffractive orders; and
a lowest diffractive order of the consecutive diffractive orders corresponds to the distance focus; and
a diffraction efficiency of the lowest diffractive order is greater than a diffraction efficiency of any other of the consecutive diffractive orders; and
the plurality of annular zones includes repeating sets of three diffractive steps.

18. The intraocular lens of claim 17, wherein the plurality of annular zones comprises at least three annular zones.

* * * * *